(12) United States Patent
Rogers et al.

(10) Patent No.: US 10,870,844 B2
(45) Date of Patent: *Dec. 22, 2020

(54) METHOD AND COMPOSITION USING A QUATERNARY AMMONIUM COMPOUND

(71) Applicant: ARCIS BIOTECHNOLOGY HOLDINGS LIMITED, Warrington (GB)

(72) Inventors: Jan Rogers, Chester (GB); Paul Reeves, Liverpool (GB); Carlos Toro Rueda, Madrid (ES)

(73) Assignee: ARCIS BIOTECHNOLOGY HOLDINGS LIMITED, Warrington (GB)

( * ) Notice: Subject to any disclaimer, the term of this patent is extended or adjusted under 35 U.S.C. 154(b) by 156 days.

This patent is subject to a terminal disclaimer.

(21) Appl. No.: 15/748,867

(22) PCT Filed: Jul. 28, 2016

(86) PCT No.: PCT/GB2016/052318
§ 371 (c)(1),
(2) Date: Jan. 30, 2018

(87) PCT Pub. No.: WO2017/017459
PCT Pub. Date: Feb. 2, 2017

(65) Prior Publication Data
US 2018/0201975 A1    Jul. 19, 2018

(30) Foreign Application Priority Data

Jul. 30, 2015 (GB) .................................. 1513492.7
Jan. 22, 2016 (GB) .................................. 1601209.8

(51) Int. Cl.
| C12Q 1/68 | (2018.01) |
| C12N 15/10 | (2006.01) |
| C12Q 1/686 | (2018.01) |
| C12Q 1/6806 | (2018.01) |
| C12Q 1/6851 | (2018.01) |

(52) U.S. Cl.
CPC ......... *C12N 15/1003* (2013.01); *C12Q 1/686* (2013.01); *C12Q 1/6806* (2013.01); *C12Q 1/6851* (2013.01); *C12Q 2521/107* (2013.01); *C12Q 2527/125* (2013.01); *C12Q 2531/113* (2013.01)

(58) Field of Classification Search
None
See application file for complete search history.

(56) References Cited

U.S. PATENT DOCUMENTS

| 5,064,613 A | 11/1991 | Higgs et al. |
| 5,300,635 A | 4/1994 | Macfarlane |
| 5,728,822 A | 3/1998 | Macfarlane |
| 10,364,427 B2 * | 7/2019 | Cobb ................. C12N 15/1003 |
| 2007/0015165 A1 | 1/2007 | Chen et al. |
| 2012/0244527 A1 | 9/2012 | Trinh et al. |
| 2012/0322058 A1 | 12/2012 | Regan et al. |
| 2014/0186821 A1 | 7/2014 | Daum et al. |

FOREIGN PATENT DOCUMENTS

| CN | 101886142 A | 11/2010 |
| WO | 2013175188 A1 | 11/2013 |
| WO | 2014122486 A1 | 8/2014 |
| WO | 2014131906 A1 | 9/2014 |
| WO | 2014155078 A1 | 10/2014 |
| WO | 2016051177 A2 | 4/2016 |

OTHER PUBLICATIONS

Search Report for Corresponding GB Application No. GB1601209.8 dated Oct. 27, 2016, 5 pages.
International Search Report and Written Opinion for PCT Application No. PCT/GB2016/052318 dated Oct. 26, 2016, 12 pages.
Farell et al. "Bovine serum albumin further enhances the effects of organic solvents on increased yield of polymerase chain reaction of GC-rich templates", BMC Research Notes, 2012, 5:257, 8 pages.
Higuchi, "Kinetic PCR Analysis: Real-time Monitoring of DNA Amplification Reactions," Bio/Technology, vol. 11, pp. 1026-1030, Sep. 1993.
International Preliminary Report on Patentability for International Application No. PCT/GB2016/052318 dated Jan. 30, 2018, 8 pages.

* cited by examiner

*Primary Examiner* — James Martinell
(74) *Attorney, Agent, or Firm* — Hoffman Warnick LLC

(57) ABSTRACT

A method of determining of the presence or absence of a target RNA component in a sample, the method comprising steps of: (a) contacting the sample with a composition comprising (i) a quaternary ammonium compound or a precursor thereof, which should extract/release the nucleic acid from the sample; (b) optionally storing and/or transporting the composition obtained in step (a); (c) contacting the composition obtained in step (a) with a composition comprising a proteinaceous washing agent, e.g. BSA or casein for stabilizing the RNA for transport and/or storage; and (d) using the composition obtained in step (c) in an amplification method, e.g. RT-PCR.

14 Claims, No Drawings

Specification includes a Sequence Listing.

SEQUENCE LISTING

<160> NUMBER OF SEQ ID NOS: 12

<210> SEQ ID NO 1
<211> LENGTH: 24
<212> TYPE: DNA
<213> ORGANISM: Artificial
<220> FEATURE:
<223> OTHER INFORMATION: Primer Protozoan Forward

<400> SEQUENCE: 1
gttaagggag tgaagacgat caga                                              24

<210> SEQ ID NO 2
<211> LENGTH: 26
<212> TYPE: DNA
<213> ORGANISM: Artificial
<220> FEATURE:
<223> OTHER INFORMATION: Primer Protozoan Reverse

<400> SEQUENCE: 2
aacccaaaga ctttgatttc tcataa                                            26

<210> SEQ ID NO 3
<211> LENGTH: 19
<212> TYPE: DNA
<213> ORGANISM: Artificial
<220> FEATURE:
<223> OTHER INFORMATION: Primer Bacterial Forward

<400> SEQUENCE: 3
ggaactggtg ccggaacgc                                                    19

<210> SEQ ID NO 4
<211> LENGTH: 19
<212> TYPE: DNA
<213> ORGANISM: Artificial
<220> FEATURE:
<223> OTHER INFORMATION: Primer Bacterial Reverse

<400> SEQUENCE: 4
gacttcgatc agtttgacg                                                    19

<210> SEQ ID NO 5
<211> LENGTH: 19
<212> TYPE: DNA
<213> ORGANISM: Artificial
<220> FEATURE:
<223> OTHER INFORMATION: Control Primer Forward

<400> SEQUENCE: 5
agatttggac ctgcgagcg                                                    19

<210> SEQ ID NO 6
<211> LENGTH: 20
<212> TYPE: DNA
<213> ORGANISM: Artificial
<220> FEATURE:
<223> OTHER INFORMATION: Control Primer Reverse

<400> SEQUENCE: 6
gagcggctgt ctccacaagt                                                   20

<210> SEQ ID NO 7
<211> LENGTH: 36
<212> TYPE: DNA
<213> ORGANISM: Artificial

```
<220> FEATURE:
<223> OTHER INFORMATION: Probe Plasmodium with 5'-FAM- and -TAMRA-3'

<400> SEQUENCE: 7
accgtcgtaa tcttaaccat aaactatgcc gactag                              36

<210> SEQ ID NO 8
<211> LENGTH: 23
<212> TYPE: DNA
<213> ORGANISM: Artificial
<220> FEATURE:
<223> OTHER INFORMATION: Probe E.coli with 5'-FAM- and -TAMRA-3'

<400> SEQUENCE: 8
cgtatcactg cgcgccacat tcg                                            23

<210> SEQ ID NO 9
<211> LENGTH: 23
<212> TYPE: DNA
<213> ORGANISM: Artificial
<220> FEATURE:
<223> OTHER INFORMATION: Probe Human with 5'-FAM/VIC- and -BHQ1-3'

<400> SEQUENCE: 9
ttctgacctg aaggctctgc gcg                                            23

<210> SEQ ID NO 10
<211> LENGTH: 19
<212> TYPE: DNA
<213> ORGANISM: Artificial
<220> FEATURE:
<223> OTHER INFORMATION: hRNaseP Forward primer

<400> SEQUENCE: 10
agatttggac ctgcgagcg                                                 19

<210> SEQ ID NO 11
<211> LENGTH: 20
<212> TYPE: DNA
<213> ORGANISM: Artificial
<220> FEATURE:
<223> OTHER INFORMATION: hRNaseP Reverse primer

<400> SEQUENCE: 11
gagcggctgt ctccacaagt                                                20

<210> SEQ ID NO 12
<211> LENGTH: 23
<212> TYPE: DNA
<213> ORGANISM: Artificial
<220> FEATURE:
<223> OTHER INFORMATION: hRNaseP Probe with 5'-VIC- and -TAMRA-3'

<400> SEQUENCE: 12
ttctgacctg aaggctctgc gcg                                            23
```

METHOD AND COMPOSITION USING A QUATERNARY AMMONIUM COMPOUND

The present invention relates to a method of detecting the presence or absence a fragment of RNA in a sample. Detection of RNA can be useful in many applications, for example in the fields of forensics and diagnostics. The present invention can find utility across these areas. The invention is particularly applicable in diagnostics and is useful in the diagnosis of infectious diseases, for example malaria, and of diseases such as cancer.

RNA can be very useful in the detection of cancer since RNA provides an up to date indication of the current status of a cell. For example, many tests for leukaemia rely on the detection of RNA. However the instability of RNA often limits its use in diagnostics. Prostate cancer is currently detected from prostate specific antigens present in a urine or tissue sample. However the test merely indicates prostate activity and does not point specifically to cancer. It is also difficult to interpret the results without a baseline reference. If the RNA also present in urine could be detected this could indicate the presence of cancer cells and provide useful information about the progress of the disease.

Malaria is typically diagnosed by detecting the presence of plasmodium in a blood sample. A number of methods are known but each has drawbacks.

One common method of diagnosing malaria is carried out by smearing blood on a glass plate and studying it under a microscope to look for plasmodia. However specialist equipment and skilled technicians are needed to examine the plates and determine a diagnosis. Unless a technician is highly skilled in the technique this method has a diagnosis threshold of about 500 parasites/µl blood.

Other currently used diagnosis methods include those based on antigen assays. Lateral flow rapid diagnosis assays can be used in the field and the result can be read as the presence or absence of a coloured strip on a dipstick. However such tests are not 100% sensitive and provide a qualitative rather than a quantitative analysis. Furthermore the threshold for diagnosis is 100 parasites/µl blood making it difficult to detect early infection.

A further method which has recently been developed involves molecular methods based on the polymerase chain reaction. One of the most reliable methods currently available is a Qiagen (RTM) method involving the detection of a DNA fragment. This is more accurate than microscopy but has a detection limit of 1-20 parasites/µl blood.

There exists a need for a method by which malaria can be accurately diagnosed when only low levels of infection and/or when small sample volumes are available.

The provision of a method by which genetic material can be readily identified from very small amounts of a sample would be highly advantageous in other areas of diagnostics, as well as in forensics.

Many current methods of diagnosis as well as forensic techniques rely on the detection of a specific DNA sequence in a sample.

Most cells contain genetic material in the form of DNA and RNA. RNA is typically present in higher concentrations as multiple copies are transcribed per copy of DNA. Furthermore RNA can often provide more accurate information on the current genetic status of a cell than DNA because it is more indicative of the particular genes that are being transcribed at any given time.

However RNA is very fragile and often degrades very quickly before amplification can be carried out. In particular it is difficult to store and transport RNA. Currently RNA must be purified prior to storage or transport. In particular RNA must be purified prior to its use in an amplification process such as a reverse transcription polymerase chain reaction (RT-PCR) where, typically, complementary DNA (cDNA) is produced from the RNA and a target sequence from the cDNA is subsequently amplified. Typically once RNA has been purified it is stored in nuclease-free water at −80° C. or at −20° C. following ethanol precipitation. However storage at such temperatures is often not possible and is inconvenient and costly. This is especially the case where samples are taken in areas such as Africa where malaria is prevalent. Ethanol precipitation has the further disadvantage that samples must be pelleted and dissolved in buffer each time a sample is required.

It is an aim of the present invention to provide improved means for identifying target sequences of RNA.

According to a first aspect of the present invention there is provided a method of determining of the presence or absence of a target RNA component in a sample, the method comprising steps of:

(a) contacting the sample with a composition comprising
   (i) a quaternary ammonium compound or a precursor thereof;
(b) optionally storing and/or transporting the composition obtained in step (a);
(c) contacting the composition obtained in step (a) with a composition comprising a proteinaceous washing agent; and
(d) using the composition obtained in step (c) in an amplification method.

The sample used in the method of the present invention may be taken from a plant or from an animal, for example a human.

In some embodiments the sample is obtained from a plant. In such embodiments the method may be used to detect whether the plant is infected with a disease or if the plant has a genetic defect.

The sample used in the method of the present invention is preferably a sample of bodily fluid or tissue obtained from a human or other animal. Preferably the sample is a sample of bodily fluid or tissue obtained from a human. Suitable bodily fluids include blood and blood components, mucus, saliva, urine, vomit, faeces, sweat, semen, vaginal secretion, tears, pus, sputum and pleural fluid. Suitable tissues include cancer cells, connective tissue cells, epithelial cells, nervous tissue cells, muscle tissue cells and endodermal, mesodermal or ectodermal cells.

It is particularly advantageous that bodily fluid or tissue samples can be used directly in the method of the present invention. For example it is possible to carry out the method of the present invention on a whole blood sample or a sputum sample.

Preferably the sample is a blood sample, for example a whole blood sample.

When the sample is obtained from a plant it may comprise a portion of the leaves, roots, stem, sap, flower, seed or fruit or the plant.

Step (a) of the method of the present invention involves contacting the sample with a composition comprising (i) a quaternary ammonium compound or a precursor thereof.

Any suitable quaternary ammonium compound may be included in component (i).

Some suitable quaternary ammonium compounds have the structure (I):

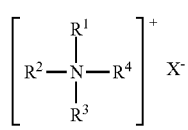
(I)

wherein each of $R^1$, $R^2$, $R^3$ and $R^4$ is an optionally substituted alkyl, alkenyl, alkylaryl or aryl group and $X^-$ is a suitable anion. Preferably each of $R^1$, $R^2$, $R^3$ and $R^4$ is an optionally substituted alkyl or alkylaryl group, more preferably an unsubstituted alkyl or alkylaryl group.

Any suitable anion $X^-$ may be used. $X^-$ may be selected from halide, acetate, nitrite, a lower alkyl sulfate, carbonate or alkyl carboxylate. Preferably $X^-$ is chloride or bromide.

Each of $R^1$, $R^2$, $R^3$ and $R^4$ may be an unsubstituted alkyl group having from 1 to 30 carbon atoms or an alkylaryl group, for example a benzyl group.

Preferably at least one of $R^1$, $R^2$, $R^3$ and $R^4$ is an unsubstituted alkyl group having at least 6 carbon atoms, preferably at least 8 carbon atoms.

In one preferred embodiment $R^1$ is an alkyl group having from 6 to 30 carbon atoms, preferably from 8 to 24 carbon atoms, suitably from 8 to 20 carbon atoms, for example from 10 to 18 carbon atoms and most preferably from 12 to 16 carbon atoms; each of $R^2$ and $R^3$ is an alkyl group having from 1 to 4 carbon atoms, preferably methyl and $R^4$ is an alkyl group having from 1 to 4 carbon atoms, preferably methyl or an alkylaryl group, preferably benzyl. The skilled person will appreciate that such compounds may often be present as a mixture of homologues.

Suitable quaternary ammonium compounds of this type include benzyldialkyl methyl ammonium chloride and dialkyl dimethyl ammonium chloride in which the alkyl groups have 10 to 24 carbon atoms.

Some preferred quaternary ammonium compounds of this type include didecyl dimethyl ammonium chloride and dimethyl benzyl alkyl ammonium chloride in which the alkyl group contains a mixture of $C_8$ to $C_{16}$ alkyl chains.

Some suitable quaternary ammonium compounds include a substituted pyridinium compound for example an alkyl or alkenyl substituted pyridinium compound. Examples include pyridinium compounds having an alkyl or alkenyl substituent of 8 to 30, preferably 10 to 20 carbon atoms.

Preferred counterions are halides. One suitable compound of this type is cetylpyridinium chloride.

Some suitable precursor compounds of this type are compounds including a guanidine moiety. The composition may comprise a compound which does not contain a permanent cation but which is protonated in solution at the pH at which the composition is used. These may be referred to as precursors to quaternary ammonium compounds. Preferred are non-polymeric guanidine compounds. Examples of such compounds include chlorhexidine salts, Chlorhexidine gluconate is especially preferred.

In some especially preferred embodiments of the method of the first aspect of the present invention the sample is contacted with a composition comprising a quaternary ammonium compound including a silicon-containing functional group. By silicon-containing group we mean to refer to any group including a silicon atom. Preferred silicon-containing functional groups are those which include a silicon atom covalently bonded via four single bonds to four organic moieties. The silicon atom may be directly bonded to oxygen and/or carbon atoms.

Preferably the method of the first aspect of the present invention component (i) comprises a compound of general formula (II):

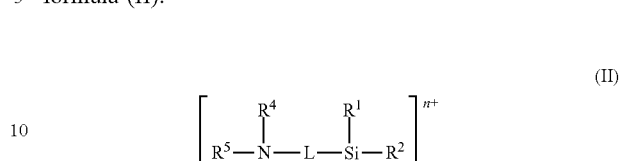
(II)

or a derivative salt thereof wherein L is a linking group; each of $R^1$, $R^2$, $R^3$, $R^5$ and $R^6$ is independently selected from H or an optionally substituted alkyl, alkenyl, aryl or alkoxy group; and n is 0 or 1.

It will be appreciated that in embodiments in which n is 1, the species shown in formula (I) is a cationic species.

In such embodiments the species of formula (I) will be present as an adduct or salt including a suitable counterion. However for ease of reference, in this document we may make general reference to compounds of formula (I) and any such reference includes where appropriate any counterion which must be present.

Any suitable counterion may be used. Monovalent counterions are preferred. Suitable counterions include halides and oxyhalo ions for example chloride, bromide, bromite, chlorite, hypochlorite, chlorate, bromate and iodate. In a most preferred embodiment the counterion is a chloride ion.

In this specification any optionally substituted alkyl, alkenyl, aryl or alkoxy group may be optionally substituted with one or more substituents selected from halo, hydroxy, nitro, mercapto, amino, alkyl, alkoxy, aryl, sulfo and sulfoxy.

Preferred substituents which may be present in the alkyl, alkenyl, aryl or alkoxy groups defined herein are halogens, in particular fluorine. In particular each of $R^1$, $R^2$, $R^3$, $R^4$, $R^5$ or $R^6$ may comprise fluoroalkyl or fluoroalkoxy groups which may comprise one or more fluorine atoms.

Each of $R^1$, $R^2$ and $R^3$ is independently selected from an optionally substituted alkyl, alkenyl, aryl or alkoxy group. Preferably at least one of $R^1$, $R^2$ and $R^3$ is an optionally substituted alkoxy group. More preferably each of $R^1$, $R^2$ and $R^3$ is an optionally substituted alkoxy group, most preferably each is an unsubstituted alkoxy group. The alkyl group of the alkoxy group may be straight chained or branched. Preferably each of $R^1$, $R^2$ and $R^3$ is an alkoxy group having from 1 to 20 carbon atoms, preferably from 1 to 16 carbon atoms, more preferably from 1 to 12 carbon atoms, preferably from 1 to 8 carbon atoms, suitably from 1 to 6 carbon atoms, more preferably from 1 to 4 carbon atoms.

In preferred embodiments each of $R^1$, $R^2$ and $R^3$ is independently selected from methoxy, ethoxy, propoxy, butoxy and isomers thereof. Most preferably each of $R^1$, $R^2$ and $R^3$ is selected from methoxy, ethoxy and isopropoxy. Preferably each of $R^1$, $R^2$ and $R^3$ is selected from methoxy and ethoxy. Most preferably each of $R^1$, $R^2$ and $R^3$ is methoxy. Preferably each of $R^1$, $R^2$ and $R^3$ is the same.

$R^4$ and $R^6$ is preferably an alkyl group having from 1 to 8 carbon atoms, most preferably 1 to 6 carbon atoms, more preferably 1 to 4 carbon atoms. $R^4$ and $R^6$ may suitably be selected from methyl, ethyl, propyl, butyl and isomers thereof. Preferably $R^4$ and $R^6$ is methyl or ethyl. Most preferably $R^4$ and $R^6$ is methyl.

Preferably R⁵ is an alkyl group having from 8 to 30 carbon atoms, for example from 10 to 26 carbon atoms, suitably from 12 to 24 carbon atoms, preferably from 14 to 22 carbon atoms, suitably from 16 to 20 carbon atoms, for example 17 to 19 carbon atoms, suitably 18 carbon atoms.

L is a linking group. It may suitably be a bond or an optionally substituted alkylene, alkenylene or arylene group. Preferably L is an optionally substituted alkenylene group. It may be substituted along the chain or within the chain. For example L may be an ether linking moiety, i.e. a group of formula $O(CH_2)_n$ in which n is 1 to 12, preferably 1 to 6.

Preferably L is an unsubstituted alkylene group, more preferably an alkylene group having 1 to 12 carbon atoms, preferably 1 to 10 carbon atoms, suitably 1 to 8 carbon atoms, for example 2 to 8 carbon atoms, more preferably 2 to 6 carbon atoms, suitably 2 to 5 carbon atoms for example 2 to 4 carbon atoms. In especially preferred embodiments L is a propylene group.

In especially preferred embodiments of the compound of formula (I), $R^1$, $R^2$ and $R^3$ are each $C_1$ to $C_4$ alkoxy, L is a $C_2$ to $C_5$ alkylene group, $R^4$ and $R^6$ are each $C_1$ to $C_4$ alkyl groups and $R^5$ is a $C_{12}$ to $C_{24}$ alkyl group.

Most preferably the compound of formula (I) is the compound shown in formula (IV). This compound is commercially available as a solution in methanol.

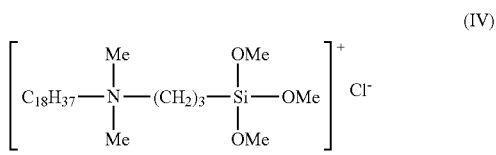

(IV)

The skilled person will appreciate that commercial sources of such compounds may include some residual starting material and other minor impurities.

Preferably component (i) is selected from quaternary ammonium salts of formula (I), pyridinium salts, guanidine salts and compounds of formula (II).

More preferably component (i) comprises a compound of formula (II).

Most preferably component (i) comprises a compound of formula (IV).

In preferred embodiments the composition contacted with the sample in step (a) of the method of the present invention further comprises (ii) a non-ionic surfactant.

Component (ii) may be selected from any suitable non-ionic surfactant. Suitable non-ionic surfactants will be known to the person skilled in the art and include alcohol ethoxylates, fatty acid esters and alkyl polyglycosides.

Non-ionic surfactants may have a hydrophilic portion, suitably an alkoxylate moiety or a sugar moiety. Suitable non-ionic surfactants include alcohol ethoxylates and fatty alcohol polyglycosides. Suitably the hydrophilic-lipophilic balance (HLB) value of a non-ionic surfactant used in the present invention is at least 7, and preferably at least 10. Especially suitable non-ionic surfactants may have an HLB value falling in the range 10-16, preferably 10-14. For the purposes of these definitions HLB value is determined by the classical method of Griffin (Griffin W C: "Calculation of HLB Values of Non-Ionic Surfactants," Journal of the Society of Cosmetic Chemists 5 (1954): 249).

Preferred non-ionic surfactants for use herein include hydrocarbyl saccharide compounds. By hydrocarbyl-saccharide compound we mean to refer to a compound including a hydrocarbyl group and a saccharide moiety.

The hydrocarbyl group may be bound to the saccharide moiety via a carbon-carbon bond or via a carbon-oxygen bond. Preferably it is bound to the saccharide moiety via a carbon-oxygen bond, for example via an ester linkage or an ether linkage. Most preferably it is bound to the oligosaccharide moiety via an ether linkage. Thus in preferred embodiments the non-ionic surfactant is a hydrocarbyl ether of a saccharide moiety.

The hydrocarbyl-saccharide compound may include one or more hydrocarbyl groups. Preferably it comprises one hydrocarbyl group. The hydrocarbyl group may be an optionally substituted alkyl, alkenyl or alkynylene group. Most preferably it is an optionally substituted alkyl group. Suitable substituents include halo, hydroxy, nitro, mercapto, amino, alkyl, alkoxy, aryl, sulfo and sulfoxy. Any substitution may be within the chain or along it, for example the chain may include an ether linkage.

Preferably the hydrocarbyl group is an unsubstituted alkyl group. It may be straight chained or may be branched. Most preferably it is straight chained. Especially preferred hydrocarbyl groups are alkyl groups having from 1 to 30 carbon atoms, preferably 2 to 24 carbon atoms, more preferably from 4 to 20 carbon atoms, suitably from 4 to 16 carbon atoms, preferably from 6 to 14 carbon atoms, for example from 6 to 12 carbon atoms and most preferably from 8 to 10 carbon atoms. Preferred are straight chained alkyl groups having from 6 to 12 carbon atoms.

The saccharide moiety of the hydrocarbyl oligosaccharide species may include from 1 to 10 monosaccharide species. Thus it may be a monosaccharide unit, a disaccharide unit or an oligosaccharide unit. Preferably the saccharide moiety comprises from 2 to 8, suitably from 2 to 6, preferably from 2 to 5, for example 3 or 4 monosaccharide units. Any suitable monosaccharide unit may be included. Preferred saccharides include allose, altrose, glucose, mannose, gulose, idose, galactose and talose.

Mixtures of two or more monosaccharides may be present in the saccharide moiety. Preferably the saccharide moiety comprises glucose. More preferably all of the monosaccharide units present in the saccharide moiety are glucose.

In a preferred embodiment the non-ionic surfactant is an alkyl polyglucoside (APG), preferably a monoalkyl-polyglucoside. Suitably the non-ionic surfactant is a compound of general formula (III):

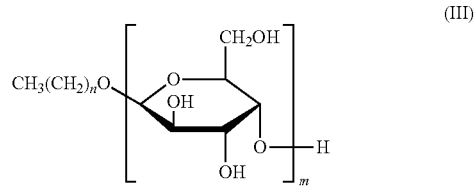

(III)

wherein n is from 5 to 12, preferably from 6 to 10, more preferably from 7 to 9 and m is from 1 to 6, preferably from 2 to 5, more preferably 3 or 4.

The composition contacted with the sample in step (a) of the method of the first aspect may be provided in any suitable form. It may consist essentially of component (i) or component (i) and a solvent. It may consist essentially of components (i) and (ii) or it may comprise one or more further components. Suitably the composition includes one or more solvents. Preferred solvents are water and water miscible solvents. In embodiments in which the quaternary ammonium compound is obtained commercially as a solution in methanol, much of the methanol is suitably removed prior to use of the compound in the method of the present invention.

Preferably the composition is aqueous. In especially preferred embodiments water comprises at least 90 wt %, more preferably at least 95 wt % or at least 99 wt % of all solvents present in the composition. In one preferred embodiment the composition is freeze dried. In such embodiments an aqueous mixture may be provided upon contact with sample. Freeze-dried compositions may be advantageous for storage and distribution.

In some embodiments the composition used in step (a) may be immobilised on a solid support, for example on a resin bead or on a planar substrate.

The composition used in step (a) of the method of the present invention may include a mixture of two or more quaternary ammonium compounds and/or a mixture of two or more non-ionic surfactants.

The composition contacted with the sample in step (a) of the method of the present invention preferably comprises at least 0.0001 wt % of a quaternary ammonium compound, preferably at least 0.0005 wt %, more preferably at least 0.001 wt %, and more preferably at least 0.002 wt %.

The quaternary ammonium compound preferably comprises up to 10 wt % of the composition contacted with the sample in step (a), suitably up to 5 wt %, preferably up to 1 wt %, preferably up to 0.1 wt %, more preferably up to 0.01 wt %, and more preferably up to 0.005 wt %.

In embodiments in which more than one quaternary ammonium compound is present, the above amounts refer to the total of all such compounds.

The non-ionic surfactant is suitably present in the composition contacted with the sample in step (a) in an amount of at least 0.0001 wt %, preferably at least 0.0005 wt %, more preferably at least 0.001 wt %, and more preferably at least 0.002 wt %.

The non-ionic surfactant may be present in the composition contacted with the sample in step (a) in an amount of up to 10 wt % of the composition, suitably up to 5 wt %, preferably up to 1 wt %, preferably up to 0.1 wt %, more preferably up to 0.01 wt %, and more preferably up to 0.005 wt %.

In embodiments in which the composition comprises two or more non-ionic surfactants the above amounts refer to the total of all such compounds.

The weight ratio of the quaternary ammonium compound functional component to the non-ionic surfactant is preferably from 1:10 to 10:1, preferably from 1:5 to 5:1, preferably from 1:3 to 3:1, suitably from 1:2.5 to 2.5:1.

The composition contacted with the sample in step (a) preferably has a pH of from 6 to 8.

The composition contacted with the sample preferably comprises (i) a quaternary ammonium compound and (ii) a non-ionic surfactant. In some embodiments the composition may consist essentially of these components.

In some embodiments the composition further includes a solvent, preferably water.

Other components may also be present, for example magnesium chloride and tris buffers. However this is not preferred.

Suitably components (i) and (ii), which may each comprise a mixture of components, together make up at least 50 wt % of all ingredients other than solvent present in the composition used in step (a), preferably at least 70 wt %, more preferably at least 90 wt %, preferably at least 95 wt %, for example at least 99 wt %.

Preferably the composition used in step (a) of the method of the present invention comprises less than 0.01 mmol of magnesium ions, preferably less than 0.001 mmol.

In step (a) of the method of the first aspect of the present invention the sample is contacted with a composition comprising (i) a quaternary ammonium compound and optionally (ii) a non-ionic surfactant. Suitably the ratio of the sample composition (e.g. blood) to the composition used in step (a) is from 10:1 to 1:1000, preferably from 5:1 to 1:100, suitably from 1:1 to 1:20 for example from 1:3 to 1:10, by volume.

Suitably the composition is agitated to ensure mixing.

Step (b) of the method of the present invention involves optionally storing and/or transporting the composition obtained in step (a). A particular advantage of the present invention is that RNA can be stabilised for much longer compared to methods of the prior art.

Step (b) may involve storing the RNA for at least 30 minutes, suitably at least 1 hour. Step (b) may involve storing the RNA for up to 6 hours, suitably up to 12 hours, for example up to 24 hours or up to 48 hours.

In some embodiments the RNA may be stored for more than 3 days, for example more than one week or more than one month.

Suitably in step (b) the composition is stored at ambient temperature. The composition is suitably stored in a sealed container but no special conditions are needed.

Step (a) suitably involves storing and/or transporting the composition directly obtained in step (a). Typically no purification steps are carried out between step (a) and step (b).

Step (c) involves contacting the composition obtained in step (a) with a composition comprising a proteinaceous washing agent.

Suitably there are no purification steps between step (a) and step (c) and the material obtained in step (a) is used directly in step (c), optionally after storing and/or transporting according to step (b).

Preferred proteinaceous washing agents are anionic proteins.

Suitable proteinaceous washing agents include tryptone, gelatin, casein and bovine serum albumin (BSA). Preferred proteinaceous washing agents include bovine serum albumin and casein. An especially preferred washing agent is BSA. Acetylated bovine serum albumin (BSA) is particularly preferred.

Suitably the proteinaceous washing agent is present in the composition used in step (c) in an amount from 0.01 to 50 wt %, preferably 0.1 to 10 wt %, suitably from 0.1 to 5 wt %, for example about 1 wt %.

Suitably the composition used in step (c) of the method of the first aspect of the present invention is an aqueous composition. Suitably water comprises at least 90 wt % of all solvents present in the composition, preferably at least 95 wt % for example at least 99 wt % of all solvents present in the composition.

In one embodiment the composition may be freeze dried. In such an embodiment an aqueous mixture may be provided upon contact with the aqueous composition obtained in step (a).

In step (c) of the method of the present invention suitably the composition obtained in step (a) is added to a composition containing the proteinaceous washing agent in a ratio of from 10:1 to 1:100, preferably from 5:1 to 1:50, suitably from 1:1 to 1:10.

It should be noted that the method of the present invention does not necessarily include using all of the mixture obtained in step (a) in step (c). In many instances a portion of the composition obtained in step (a) is contacted with the composition comprising the proteinaceous washing agent in step (c).

Suitably in step (c) of the method of the present invention the mixture is briefly agitated at room temperature. It may be left for a period of 1 second to 24 hours, suitably 5 seconds to 1 hour, preferably 5 seconds to 30 minutes, preferably 10 seconds to 10 minutes, suitably from 30 seconds to 5 minutes, for example about 1 minute.

It has been surprisingly found that the mixture obtained in step (c) of the present invention can be used directly in step (d).

It is highly advantageous that the method of the present invention provides a simple process in which RNA suitable for amplification can be obtained directly from whole blood.

In some preferred embodiments there are no washing or other purification steps between step (c) and (d).

Preferably step (d) is carried out immediately after step (c).

Step (d) involves using the composition obtained in step (c) in an amplification method.

Suitable amplification methods include polymerase chain reaction (PCR) methods and isothermal amplification methods. Examples of suitable isothermal amplification methods include loop-mediated isothermal amplification (LAMP), strand displacement amplification (SDA), helicase-dependent amplification (HDA) and nicking enzyme amplification reaction.

Suitably the amplification method is a reverse transcript PCR method. Suitable PCR methods include reverse transcription PCR (RT-PCR), endpoint reverse transcription PCR, quantitative reverse transcription (qRT-PCR), and high-fidelity reverse transcript PCR.

The method of the present invention is used to determine the presence or absence of a target RNA component. The skilled person will appreciate that in the above PCR methods it is first necessary to transcribe the RNA into cDNA that can be used in PCR.

In some preferred embodiments, the PCR method is reverse transcription PCR (RT-PCR) or quantitative reverse transcription (qRT-PCR). For example in reverse transcription PCR (RT-PCR) RNA is first converted into complementary DNA (cDNA) using a reverse transcriptase and the cDNA is then amplified using PCR. In quantitative reverse transcription PCR the amplification of the cDNA is monitored in real time, i.e. during the PCR reaction.

In preferred embodiments step (d) involves amplifying cDNA reverse transcribed from RNA present in the mixture obtained in step (c) in a reverse transcription PCR (RT-PCR).

More preferably step (d) involves amplifying and indicating the level of cDNA reverse transcribed from RNA present in the mixture obtained in step (c) in a quantitative reverse transcription PCR (qRT-PCR).

Suitably the mixture obtained in step (c) is used directly in a reverse transcription PCR (RT-PCR) or a quantitative reverse transcription PCR (qRT-PCR) without further purification of the RNA fraction. This offers significant advantages over methods of the prior art in which complex, expensive and time-consuming purification methods are often necessary. The use of the mixture obtained in step (c) directly in step (d) without further purification or processing means that diagnosis can be achieved in a shorter time using a less expensive process. Furthermore because there is little degradation of RNA in the sample following step (a) of the method of the present invention, much lower levels of detection can be achieved, enabling an earlier diagnosis.

In addition because the composition obtained in step (a) is stable to storage samples do not need to be analysed immediately. This means that multiple samples can be collated and then a single PCR process can be carried out on the multiple samples. The analysis of multiple samples in PCR can provide economies of scale. Thus the method of the present invention can lead to significant cost savings in diagnostics.

The RNA may be any suitable type of RNA. Suitable examples of RNA include messenger RNA (mRNA), micro RNA (miRNA) ribosomal RNA (rRNA), signal recognition particle RNA (SRP RNA), transfer RNA (tRNA) or transfer messenger RNA (tmRNA). Preferably, the RNA is mRNA.

Suitably step (d) involves amplifying cDNA reverse transcribed from RNA present in the mixture obtained in step (c) in a reverse transcription PCR (RT-PCR) or a quantitative reverse transcription PCR (qRT-PCR). This may be carried out using a one step or a two step process. For example in a one step reverse transcription PCR (qRT-PCR), reverse transcription of RNA to produce cDNA and amplification of a DNA target sequence by PCR is carried out in one step in a single test tube. For example in a two step reverse transcription PCR (qRT-PCR), reverse transcription of RNA to produce cDNA is carried out in a first step and amplification of a DNA target sequence by PCR is carried out in a second step.

Preferably step (d) involves the addition of at least one reagent for performing the reverse transcription PCR (RT-PCR) or quantitative reverse transcription PCR (qRT-PCR). Suitably the at least one reagent is added to the mixture obtained in step (c).

Preferably the at least one reagent is selected from: DNA polymerase, reverse transcriptase, buffer, dNTPs, or a source of magnesium. Suitably in a one step reverse transcription PCR (RT-PCR) or quantitative reverse transcription PCR (qRT-PCR) step (d) comprises the addition of all of these components, referred to as a PCR master mix. Suitably in a two step reverse-transcription PCR (qRT-PCR) step (d) comprises the addition of reverse transcriptase, buffer and dNTPs in a first step followed by the addition of a PCR master mix in a second step.

The PCR master mix may suitably be sourced from any manufacturer. However preferably the Taqman® Master Mix from Applied Biosystems, the Promega M7502 mix or the Roche Master Superscript® is used.

Preferably the DNA polymerase is a Taq DNA polymerase. Preferably the dNTPs include dATP, dGTP, dTTP, and dCTP in equal quantities. Preferably the source of magnesium is magnesium chloride. Preferably the buffer is any suitable buffer with a pH of 8.5

Preferably step (d) further comprises detecting the presence and indicating the level of a control RNA. The control RNA may be an internal control (endogenous RNA) or an exteneral control (exogenous RNA), for example a synthetic control. Suitably the control RNA is definitively present within the biological sample. When the sample is of plant origin, the control RNA is suitably a plant RNA. Preferably the control RNA is a human RNA when the biological sample is of human origin, or an animal RNA when the biological sample is of animal origin. More preferably the control RNA is a human RNA, preferably the control human RNA is of a housekeeping gene or genes that are substantially conserved in human RNA, more preferably the control human RNA is the RNAse-P gene. It will be appreciated by a person skilled in the art that the control RNA is transcribed to cDNA and the amount of cDNA which is then amplified during the PCR is detected.

Suitably therefore, a control primer pair and probe are added to the sample obtained in step (c) together with the test primers. Suitably in embodiments in which the sample is of human origin the primer pair of SEQ ID NO.5 and 6 together with the probe of SEQ ID NO. 9 are used. Suitably the relevant sequences are as follows:

```
Control Primer Forward:
                                    (SEQ ID NO. 5)
5'-AGATTTGGACCTGCGAGCG-3'

Control Primer Reverse:
                                    (SEQ ID NO. 6)
5'-GAGCGGCTGTCTCCACAAGT-3'

Probe Human:
                                    (SEQ ID NO. 9)
5'-FAM/VIC-TTCTGACCTGAAGGCTCTGCGCG-BHQ1-3'
```

Other human control primers and animal and plant primers are available and the selection of these is within the competence of the person skilled in the art.

Suitably the test primer pairs and/or probes added during at step (d) of the method are specific to the cDNA reverse transcribed from the target RNA component being detected.

Suitably the test primer pairs and/or probes added at step (d) of the method are specific to the type of microorganism(s) being identified.

In one embodiment the test primer pairs and/or probes added at step (d) of the method are specific to the identification of protozoan RNA. In one preferred embodiment the primer pairs and/or probes added at step (d) of the method are specific to the identification of Plasmodium RNA. Suitably the primer pair of SEQ ID NO.1 and 2 together with the probe of SEQ ID NO. 7 are used for identifying protozoan RNA, more specifically for identifying Plasmodium RNA. Suitably the relevant sequences are as follows:

```
Primer Protozoan Forward:
                                    (SEQ ID NO. 1)
5'-GTTAAGGGAGTGAAGACGATCAGA-3'

Primer Protozoan Reverse:
                                    (SEQ ID NO. 2)
5' AACCCAAAGACTTTGATTTCTCATAA-3'

Probe Plasmodium:
                                    (SEQ ID NO. 7)
5'-FAM-ACCGTCGTAATCTTAACCATAAACTATGCCGACTAG-
TAMRA-3'
```

Accordingly in one embodiment the method of the present invention may be used to detect the presence or absence of a target RNA sequence from Plasmodium.

In one embodiment the primer pairs and/or probes added at step (d) of the method are specific to the identification of bacterial RNA. In one preferred embodiment the primer pairs and/or probes added at step (d) of the method are specific to the identification of *Escherichia* RNA. Suitably the primer pair of SEQ ID NO.3 and 4 together with the probe of SEQ ID NO.8 are used for identifying bacterial RNA, more specifically for identifying *Escherichia* RNA. Suitably the relevant sequences are as follows:

```
Primer Bacterial Forward:
                                    (SEQ ID NO. 3)
EcoF 5'-GGAACTGGTGCCGGAACGC-3'

Primer Bacterial Reverse:
                                    (SEQ ID NO. 4)
5'-GACTTCGATCAGTTTGACG-3'
```

```
                        -continued
Probe E. coli:
                                    (SEQ ID NO. 8)
5'-FAM-CGTATCACTGCGCGCCACATTCG-TAMRA-3'
```

In one embodiment the primer pairs and/or probes added at step (d) of the method of the present invention are specific for the identification of an RNA component which is indicative of cancer.

For example the primer pairs and/or probes may be specific for the identification of an RNA component which is indicative of leukaemia. Primer pairs and probes of this type are known and the selection of these would be within the competence of the skilled person.

The primer pairs and/or probes may be specific for the identification of an RNA component which is indicative of prostate cancer. Primer pairs and probes of this type are known and the selection of these would be within the competence of the skilled person.

Prostate cancer is currently detected from prostate specific antigens present in a urine or tissue sample. However the test merely indicates prostate activity and does not point specifically to cancer. It is also difficult to interpret the results without a baseline reference. If the RNA also present in urine could be detected this could indicate the presence of cancer cells and provide useful information about the progress of the disease. The method of the present invention ensures RNA is stabilised to facilitate detection. The detection of RNA rather than antigens may allow earlier detection of prostate cancer.

The primer pairs and/or probes may be specific for the identification of an RNA component which is indicative of breast cancer, liver cancer or colon cancer. Primer pairs and probes of this type are known and the selection of these would be within the competence of the skilled person.

The primer pairs and/or probes may be specific for the identification of an RNA component which is indicative of an oncagenic virus, for example EBV.

Because RNA provides up to date information about the status of a cell the detection of specific types of RNA may be used to provide information about the progression of a disease, for example cancer.

The detection of RNA according to the invention could also be used to ascertain how a patient is responding to a particular course of treatment. This could be useful for example in relation to a disease such as ascites.

Suitably step (d) involves a quantitative reverse transcription PCR (qRT-PCR) step. This is suitably carried out using standard procedures known in the art and using standard machinery known in the art. qRT-PCR is described in Higuchi R et al. Kinetic PCR analysis: Real time Monitoring of DNA amplification reactions. Bio/Technology 1993; 11:1026-30.

Suitably the amplification of cDNA produced from reverse transcription of RNA present in the mixture obtained in step (c) is conducted by a set program of heating cycles during reverse transcription PCR (RT-PCR) quantitative reverse transcription PCR (qRT-PCR) as is known in the art. The heating cycle may comprise any of the following stages: mix activation, initial reverse transcription, initial denaturation, denaturation, annealing, extension, final extension, or cooling. Suitably the heating cycle comprises at least initial denaturation, denaturation, and annealing. In some embodiments, the heating cycle comprises at least an initial reverse transcription, initial denaturation, denaturation and annealing. It will be appreciated by a person skilled in the art that an initial reverse transcription step will not be required if the RNA has been transcribed to cDNA in a separate first step. Optionally, any of the stages may be repeated, alone or in combination with any other stage. Preferably the denaturation and annealing stages are repeated, more preferably these stages are repeated for between 25 and 55 cycles, more preferably for between 30 and 45 cycles.

In one embodiment, the heating cycle comprises the following:

| Initial reverse transcription | 45° C. 10 min | |
|---|---|---|
| Initial denaturation | 95° C. 10 min | |
| Denaturation | 95° C. 15 sec | |
| Annealing | 60° C. 60 sec | 45 cycles |

Preferably this heating cycle is used when conducting quantitative reverse transcription PCR (qRT-PCR).

In another embodiment, the heating cycle comprises the following:

| Initial reverse transcription | 45° C. 10 min | |
|---|---|---|
| Initial denaturation | 94° C. 5 min | |
| Denaturation | 94° C. 20 sec | |
| Annealing | 54° C. 20 sec | 30 cycles |
| Extension | 72° C. 30 sec | |
| Final extension | 72° C. 5 min | |
| Cooling | 10° C. ∞ | |

Preferably this heating cycle is used when conducting any other type of PCR, for example endpoint reverse transcription PCR.

Optionally, the method of the first aspect may further comprise a step of analysing the PCR products of step (d) by electrophoresis, preferably agarose gel electrophoresis. Methods of conducting such analyses are well known in the art.

Preferred embodiments of the present invention involve using the previously identified combinations of primer pairs and probes to determine the presence or absence of the RNA target component. The use of the probe allows visualisation of the PCR products as they are produced during PCR in step (d) of the method. The probes act to bind to the PCR products when they recognise the specific organism DNA they are complementary to, and as that PCR product is replicated during the PCR process, the probes increase in fluorescence. This fluorescence is visualised with the aid of graphical representation to indicate the detection of specific cDNA reverse transcribed from RNA within the sample undergoing PCR.

However it is also within the scope of the invention to use an alternative visualisation method.

Thus the present invention may further comprise a step (e) of visualising the amplification products of step (d).

By the term 'visualisation' as used herein, it is meant that the amplification products of step (d) are manipulated such that they can be detected and such that the source of the RNA contained in the amplification products can be identified directly from the amplification products themselves. In some embodiments step (d) involves PCR and step (e) involves visualisation of the products of PCR. In some embodiments an alternative amplification method may be used in step (d) and step (e) may involve visualising the product of this alternative method. Alternative methods include isothermal amplification and LAMP is especially preferred.

Some preferred visualisation methods involves the use of probes and detection of fluorescence. Other visualisation method may examine an increase in turbidity or a colour change. For example a chromogenic substrate may be used to indicate the level of completion of a reaction. Visualisation methods may be a qualitative or quantitative. Suitable methods will be known to the person skilled in the art.

In one embodiment step (e) may involve visualisation of the PCR products using electrophoresis, suitably gel electrophoresis, preferably agarose gel electrophoresis. Suitably, as is known in the art, the PCR products are mixed with an intercalating agent, such as for example ethidium bromide and suitably the mixture is injected into wells in the gel before the application of a current thereto. In such an embodiment, step (e) involves using any type of PCR to amplify the DNA produced from reverse transcription of RNA present in the mixture obtained in step (c), but preferably end-point PCR. Advantageously therefore the identification of DNA contained in the PCR products is able to performed quickly after the PCR, and this embodiment may allow the method to be used with any type of PCR using a wide variety of fluorescent markers.

Suitably in such an embodiment, the requirements for conducting the PCR are the same as set out above in relation to quantitative PCR, specifically the components required for the PCR of step (d) and the heating cycle specifications.

The method of the present invention involves determining the presence or absence of a target RNA component in a sample. Suitably, the RNA target component may be a RNA component of a plant cell, a human or an animal cell or may be a RNA component of a microorganism.

In some embodiments, the RNA target component is a RNA component of a microorganism.

Preferably the microorganism/s are pathogenic microorganism/s, more preferably pathogenic prokaryotic and/or eukaryotic microorganism/s, still more preferably pathogenic bacteria or protozoa. Accordingly, the method of the first aspect may be considered a method for diagnosing a disease in a subject on the basis of identification of the relevant pathogenic microorganism/s from the biological sample acquired therefrom.

Preferably the pathogenic bacteria are selected from of the genera *Bacteroides, Bartonella, Bordetella, Borrelia, Brucella, Campylobacter, Chlamydia, Escherichia, Francisella, Haemophilus, Helicobacter, Klebsiella, Legionella, Leptospira, Moraxella, Neisseria, Pasteurella, Proteus, Pseudomonas, Salmonella, Shigella, Spirillum, Streptobacillus, Treponema, Vibro, Yersinia, Actinomyces, Bacillus, Clostridium, Corynebacterium, Listeria, Nocardia, Peptostreptococcus, Propionibacterium, Staphylococcus, Streptococcus*, or *Streptomyces*. Most preferably the pathogenic bacterium is *Escherichia coll*.

Preferably the pathogenic protozoa are selected from the genera *Acanthamoeba, Ancylostoma, Ascaradia, Babesia, Balamuthia, Balantidium, Brugia, Clonorchis, Cryptosporidium, Dicrocoelium, Dicytocaulus, Dientamoeba, aphylobothrium, Dirofilaria, Echinococcus, Echinostoma, Entamoeba, Enterobius, Fasciola, Fascioloides, Giardia, Hymenolepsis, Isospora, Leishmania, Mesocestoides, Moniezia, Necator, Naegleria, Onchocerca, Opisthorchis, Paragonimus, Plasmodium, Rhabditida, Schistosoma, Spirurida, Strongyloides, Taenia, Trichomonas, Trichuris, Toxocara, Trypanosoma, Uncinaria* or *Wuchereria*. Most preferably the pathogenic protozoa is selected from *Plasmodium falciparum, Plasmodium vivax, Plasmodium ovale*, or *Plasmodium malariae*.

In some embodiments of the present invention the target RNA component is present in a microorganism. Thus the presence of the target component RNA component is indicative that the sample is infected with the microorganism.

When the microorganism is a pathogenic microorganism the presence of the target RNA component is indicative of infection with a pathogenic disease.

The method of the present invention may be used in a method of diagnosing infection with any pathogenic disease in which a target RNA component characteristic of the pathogen can be identified.

The method of the present invention may be used to identify pathogenic infections in humans and animals. It may also be used to identify pathogenic infections in plants.

In some embodiments the target RNA component is indicative of cancer. Such a target RNA component may be an RNA component of a cancer cell or it may be exogenous RNA that is indicative of cancer.

In some embodiments, the RNA target component is an RNA component of a human or animal cell. Suitable cells include cancer cells, connective tissue cells, endocrine gland cells, muscle cells, blood cells and skin cells. The cells may be obtained from the human or animal by biopsy or by specific pathological collection. This will depend on the particular disease.

Suitable examples of cancers include, but are not limited to, breast cancer and cancers derived from brain cells, epithelial cells (carcinoma), connective tissue (sarcoma), hematopoietic cells (lymphoma and leukemia), pluripotent cells (germ cell tumour), and embryonic tissue (blastoma).

In some embodiments the human or animal cells may be indicative of an autoimmune disease. Autoimmune diseases commonly affect organ and tissue types such as blood vessels, connective tissues, endocrine glands, joints, muscles, red blood cells, and the skin. Examples of autoimmune disorders include, but are not limited to, Addison's disease, celiac disease, dermatomyositis, Graves' disease, Guillan-Barre disease, inflammatory bowel disease, multiple sclerosis, pernicious anaemia, psoriasis, rheumatoid arthritis, systemic lupus erythematosus and type I diabetes.

The present invention relates to a method of determining the presence or absence of a target RNA component in a sample. Suitably the target RNA component is present in a human or animal cell. Thus the presence of the target RNA component is indicative that the sample proider has a disease.

When the human or animal has a disease the presence of the target RNA component is indicative of said disease.

The method of the present invention may be used in a method of diagnosing any disease in which a target RNA component characteristic of the disease can be identified.

A particular advantage of the present invention is that because RNA is detected rather than genomic DNA from the cell infection can be detected at much lower levels. This enables earlier and more accurate diagnosis to be achieved. Furthermore this reduces the likelihood of either of false negative or false positive results being obtained.

Furthermore RNA provides more accurate information on the current status of a cell and can thus provide a genetic fingerprint of a disease any point in time. This may be particularly useful in tracking disease progression.

RNA is typically present in bodily fluids and tissues much higher concentrations than DNA and thus the detection of RNA rather than DNA allows much lower levels of infection with a pathogen to be detected. This may mean that the nature of a particular pathogen can be identified earlier ensuring the correct treatment can be commenced earlier. In the case of bacterial infections, early diagnosis can ensure that a correct antibiotic is used as soon as possible. This can reduce the overuse of broad spectrum antibodies—a serious problem that contributes to resistance. It can also help prevent serious infections such as sepsis developing.

The detection of RNA can also be useful in the diagnosis of cancer. RNA indicative of a cancerous growth can be detected much earlier than cancer can be detected using current clinical techniques. For example a tumour must be of a certain size for it to be detected by physical examination. Advantageously RNA can be detected from a blood or urine sample which is less intrusive than many biopsies.

The present invention is particularly useful in the diagnosis of malaria.

The limit of detection for infection with malaria using the method of the present invention is much lower than methods of the prior art. Typically the method of the invention may allow detection of malaria at less than 10 parasites/µl blood, for example less than 5 parasites/µl blood.

The method of the present invention involves the detection of a target RNA component. In some preferred embodiments the invent also involves detection of DNA present in the sample. In the method of the invention RNA is typically transcribed into cDNA and then amplified. This cDNA is identical to the genomic DNA from which the RNA has been produced. The amplification may thus involve amplification of both the cDNA and the genomic DNA.

The invention will now be further defined with reference to the following non-limiting examples.

EXAMPLE 1

Composition A was prepared comprising, in an aqueous solution:

0.003 wt % of a quaternary ammonium compound having the formula:

$$\left[ C_{18}H_{37} - \overset{\overset{\displaystyle Me}{|}}{\underset{\underset{\displaystyle Me}{|}}{N}} - (CH_2)_3 - \overset{\overset{\displaystyle OMe}{|}}{\underset{\underset{\displaystyle OMe}{|}}{Si}} - OMe \right]^+ Cl^-$$

0.003 wt % of an alkyl polyglucoside alkyl polyglucoside comprising a mixture of isomers of formula:

$$H-\left[O\underset{OH}{\underset{OH}{\bigcirc}}\right]-\left[O\underset{OH}{\bigcirc}\right]_m-O(CH_2)_nCH_3$$

where n=7 or 9 and m=1 to 5; and

Composition B was prepared comprising water and 1 wt % acetylated bovine serum albumin (BSA).

EXAMPLE 2

One blood sample was collected using an ISO-compliant tube for diagnostic containing EDTA. The fresh sample (350 µL) was extracted according to the RNA-pure system in the Qiagen (RTM) EZ-1 automated and self-contained robot, following the manufacturer's standard protocol and obtaining 50 µl of concentrated extract. 5 µl of this sample was used in a Qiagen standard qRT-PCR giving a count of 25.75. The blood sample was then stored at −20° C.

Sample 2A

30 µl of defrosted whole blood were mixed with 3 µl of composition A and 167 µl of water (molecular biology grade). The mix was vortexed and incubated at room temperature 1 minute.

2.5 µL of sample 2A was mixed with 10 µL of composition B. A RT-qPCR for *Plasmodium* spp. was then performed in the StepOne Real-Time PCR System (Applied Biosystems) with the following thermal profile:

|  | Temperature | Time | No. cycles |
| --- | --- | --- | --- |
| Initial step for reverse transcription | 45° C. | 10 min | 1 cycle |
| Initial denaturation | 95° C. | 10 min | 1 cycle |
| Denaturation | 95° C. | 15 sec | 45 cycles |
| Annealing | 60° C. | 60 sec |  |

The following mastermixes were used:

| Mastermix 1 (reverse transcription (RT) mix boosted with RT enzyme mix) | |
| --- | --- |
| Component | Amount |
| AgPath-ID$^{TM}$ One-Step RT-PCR 25x enzyme mix | 15 µl |
| NZY qPCR 2x mastermix (Nzytech) | |
| 0.1 µM forward primer (5'-GTTAAGGGAGTGAAGACGATCAGA-3' (SEQ ID NO. 1)) | |
| 0.1 µM reverse primer (5' AACCCAAAGACTTTGATTTCTCATAA-3' (SEQ ID NO. 2)) | |
| 0.05 µM forward control primer (hRnaseP) | |
| 0.05 µM reverse control primer (hRnaseP) | |
| 0.1 µM *Plasmodium* probe (5'-FAM-ACCGTCGTAATCTTAACCATAAACTAT GCCGACTAG-TAMRA-3' (SEQ ID NO. 7)) | |
| 0.02 µM internal control probe | |

| Mastermix 2 (standard reverse transcription (RT) mix) | |
| --- | --- |
| Component | Amount |
| AgPath-ID$^{TM}$ One-Step RT-PCR 25x enzyme mix and Buffer RT | 15 µl |
| 0.1 µM forward primer (5'-GTTAAGGGAGTGAAGACGATCAGA-3' (SEQ ID NO. 1)) | |
| 0.1 µM reverse primer (5' AACCCAAAGACTTTGATTTCTCATAA-3' (SEQ ID NO. 2)) | |
| 0.05 µM forward control primer (hRnaseP) | |
| 0.05 µM reverse control primer (hRnaseP) | |
| 0.1 µM *Plasmodium* probe (5'-FAM-ACCGTCGTAATCTTAACCATAAACTAT GCCGACTAG-TAMRA-3' (SEQ ID NO. 7)) | |
| 0.02 µM internal control probe | |

| Mastermix 3 (standard qPCR enzyme mix; non-reverse transcription (RT)) | |
| --- | --- |
| Component | Amount |
| NZY qPCR 2x mastermix (Nzytech) | 15 µl |
| 0.1 µM forward primer (5'-GTTAAGGGAGTGAAGACGATCAGA-3' (SEQ ID NO. 1)) | |
| 0.1 µM reverse primer (5' AACCCAAAGACTTTGATTTCTCATAA-3' (SEQ ID NO. 2)) | |
| 0.05 µM forward control primer (hRnaseP) | |
| 0.05 µM reverse control primer (hRnaseP) | |
| 0.1 µM *Plasmodium* probe (5'-FAM-ACCGTCGTAATCTTAACCATAAACTAT GCCGACTAG-TAMRA-3' (SEQ ID NO. 7)) | |
| 0.02 µM internal control probe | |

Mastermix 1 will amplify both DNA and RNA present in the sample; mastermix 2 will amplify only RNA and mastermix 3 will amplify only the DNA.

The control primers and probe are as follows:

hRNaseP Forward primer (SEQ ID NO. 10)
AGATTTGGACCTGCGAGCG hRNaseP Reverse primer (SEQ ID NO. 11)
GAGCGGCTGTCTCCACAAGT hRNaseP Probe (SEQ ID NO. 12)
VIC-TTCTGACCTGAAGGCTCTGCGCG-TAMRA The results of the PCR (counts) are shown in table 1:

TABLE 1

|  | Mastermix 1 | Mastermix 2 | Mastermix 3 |
| --- | --- | --- | --- |
| Sample 2A (inv) | 17.43 | 19.64 | 22.71 |

The results show that detection of RNA according to the present invention allows lower levels of plasmodium to be detected compared to the detection of DNA only and shows a significant improvement over the Qiagen standard procedure. It should also be noted that the method of the present invention uses only 30 µL of the blood whereas the Qiagen method uses 350 µL. This represents a substantial benefit for example in diagnosis as many more tests (eg for different diseases) can be carried out on the same amount of blood.

Sample 2A was split and stored at either room temperature for 26 days (624 h) or −20° C. for 6 days (144 h). The PCR experiments were repeated after 24 h, 48 h, 144 h and 624 h. The results are shown in table 2.

|  | Mastermix 1 | Mastermix 2 | Mastermix 3 |
| --- | --- | --- | --- |
| 24 h, room temp | 17.38 | 19.69 | 21.82 |
| 24 h, −20° C. | 17.66 | 19.46 | 22.51 |
| 48 h, room temp | 18.25 | 21.4 | 23.14 |
| 48 h, −20° C. | 17.74 | 20.61 | 23.22 |
| 144 h, room temp | 18.76 | 21.36 | 22.95 |
| 144 h, −20° C. | 19.69 | 22.31 | 23.24 |
| 624 h, room temp | 19.35 | 22.67 | No amplification |

These results show how the method of the present invention still allows RNA to be detected following storage.

The invention claimed is:

1. A method of determining of the presence or absence of a target RNA component in a sample, the method comprising steps of:
(a) contacting the sample with a composition comprising
   (i) a quaternary ammonium compound;
(b) storing and/or transporting the composition obtained in step (a);
(c) contacting the composition obtained in step (a) with a composition comprising a proteinaceous washing agent; and
(d) carrying out an amplification method on the composition obtained in step (c),
wherein step (d) includes amplifying and indicating a level of cDNA reverse transcribed from RNA present in the composition obtained in step (c) in a quantitative reverse transcription PCR (qRT-PCR).

2. A method according to claim 1 wherein the sample is a sample of bodily fluid or tissue obtained from a human.

3. A method according to claim 1 wherein in step (a) the sample is contacted with a composition comprising a quaternary ammonium compound including a silicon-containing functional group.

4. A method according to claim 1 wherein the composition contacted with the sample in step (a) of the method of the present invention further comprises (ii) a non-ionic surfactant.

5. A method according to claim 4 wherein the non-ionic surfactant is an alkyl polyglucoside.

6. A method according to claim 1 wherein step (b) involves storing the RNA for up to 48 hours.

7. A method according to claim 1 wherein in step (b) the composition is stored at ambient temperature.

8. A method according to claim 1 wherein the composition obtained from step (a) is not purified prior to step (b).

9. A method according to claim 1 wherein the composition obtained from step (a) is not purified prior to step (c).

10. A method according to claim 1 wherein the proteinaceous washing agent is selected from bovine serum albumin and casein.

11. A method according to claim 1 wherein step (d) is carried out immediately after step (c).

12. A method according to claim 1 which further includes a step (e) of visualising the amplification products of step (d).

13. A method according to claim 1 wherein the target RNA component is indicative of a disease.

14. A method according to claim 13 wherein the disease is an infectious disease or cancer.

* * * * *